(12) United States Patent
Grönlund (10) Patent No.: US 11,360,079 B2
(45) Date of Patent: Jun. 14, 2022

(54) T-CELL REACTIVITY PLATFORM

(71) Applicant: NEOGAP Therapeutics AB, Stockholm (SE)

(72) Inventor: Hans Grönlund, Lidingö (SE)

(73) Assignee: NEOGAP Therapeutics AB, Stockholm (SE)

( * ) Notice: Subject to any disclaimer, the term of this patent is extended or adjusted under 35 U.S.C. 154(b) by 722 days.

(21) Appl. No.: 16/061,611

(22) PCT Filed: Dec. 15, 2016

(86) PCT No.: PCT/EP2016/081141
§ 371 (c)(1),
(2) Date: Jun. 12, 2018

(87) PCT Pub. No.: WO2017/102921
PCT Pub. Date: Jun. 22, 2017

(65) Prior Publication Data
US 2020/0309764 A1    Oct. 1, 2020

(30) Foreign Application Priority Data

Dec. 16, 2015  (EP) .................................. 15200619
Apr. 12, 2016  (SE) .................................. 1650493-8

(51) Int. Cl.
*G01N 33/50* (2006.01)
*G01N 33/564* (2006.01)
*C12N 5/0783* (2010.01)

(52) U.S. Cl.
CPC ......... *G01N 33/505* (2013.01); *G01N 33/502* (2013.01); *G01N 33/564* (2013.01); *C12N 5/0636* (2013.01); *G01N 2333/52* (2013.01); *G01N 2500/10* (2013.01)

(58) Field of Classification Search
CPC ............... G01N 33/505; G01N 33/502; G01N 33/564; G01N 2500/10
See application file for complete search history.

(56) References Cited

U.S. PATENT DOCUMENTS

| 6,218,132 B1 | 4/2001 | Spack et al. |
| 2005/0095298 A1 | 5/2005 | Gronlund |

FOREIGN PATENT DOCUMENTS

| CN | 101614734 | 12/2009 |
| CN | 101646693 | 2/2010 |
| CN | 102978260 | 3/2013 |
| CN | 104144939 | 11/2014 |
| EP | 1356826 | 10/2003 |
| WO | WO 2003/070909 | 8/2003 |
| WO | WO 2005/010026 | 2/2005 |
| WO | WO 2008/104811 | 9/2008 |
| WO | WO 2013/127816 | 9/2013 |

OTHER PUBLICATIONS

Serdakowski et al, 2012. Bioctechnol J. 7:1509-1516.*
Bronge et al (2019. MethodsX. 1635-1641).*
Tan et al. 2006, Journal of Chromatography A, 1141: 226-234.*
Gagnon et al, 2017, BioProcess International, 10 pages as printed; available at https://bioprocessintl.com/downstream-processing/separation-purification/recent-advances-in-endotoxin-removal-an-upgrade-to-a-traditional-method-and-a-new-adsorption-chemistry/.*
Turner et al (2001. Journal of Immunological Methods. 256: 107-119).*
Velickovic et al (2008. Int Arch Allergy Immunol. 146: 1-10).*
Morita et al (2012. International Journal of Molecular Medicine. 29: 153-158).*
Andersson et al., "A Novel adjuvant-allergen complex, CBP-rFe1 d 1, induces up-regulation of CD86 expression and enhances cytokine release by human denritic cells in vitro", Immunology 1113:253-259, 2004.
European Search Report in Application No. 15200619.3, dated Mar. 31, 2016, 12 pages.
Gronlund et al., "Carbohydrate-based particles: a new adjuvant for allergen-specific immunotherapy", Immunology 107: 523-529, 2002.
Gronlund et al., "Diagnosis and treatment of IgE-mediated allergy: new approaches using recombinant allergens", Stockholm 2005.
Internation Search Report in Internation Application No. PCT/EP2016/081141, dated Feb. 17, 2017, 13 pages.
Ito et al., "Combinatorial contextualization of peptidic epitopes for enhanced cellular immunity", PLOS One, vol. 9, issue 10, e110425, 2014.
Li et al., "Endotoxin contamination: a key element in the interpretation of nanosafety studies", 11(3), 269-287, 2016.
Lindskog et al., "Selection of protein epitopesfor antibody production.", Biotechniques, 38(5): 723-7, 2005.
Matzelle et al., "Humoral immune responses to model antigen co-delivered with biomaterials used in tissue engineering", Biomaterials 25: 295-304, 2004.
Neimert-Andersson et al., "Carbohydrate-based particles reduce allergic inflammation in a mouse model for cat allergies", Allergy 63:518-526, 2008.
Reichelt et al., "Single step protocol to purify recombinant proteins with low endotoxin contents", Protein Expression and Purification 46: 483-488, 2006.

(Continued)

*Primary Examiner* — Zachary C Howard
(74) *Attorney, Agent, or Firm* — Fish & Richardson P.C.

(57) ABSTRACT

Methods for assaying antigen-specific T-cell activation in vitro, comprising the steps of (a) providing a phagocytable particle, having a candidate antigen polypeptide tightly associated thereto, wherein the particle with the associated polypeptide has been subjected to a denaturing wash resulting in an endotoxin level low enough to not interfere with the subsequent steps; (b) providing a viable antigen-presenting cell; (c) contacting the washed particle with the antigen-presenting cell under conditions allowing phagocytosis of the particle by the antigen-presenting cell; (d) providing a T-cell sample to be assayed comprising viable T-cells; (e) contacting the T-cell sample with the antigen-presenting cell contacted with the particle under conditions allowing specific activation of T-cells in response to an antigen presented by an antigen-presenting cell; and (f) determining the degree of T-cell activation in the T-cell sample.

19 Claims, 7 Drawing Sheets

(56) References Cited

OTHER PUBLICATIONS

Sedra, "Praticke platforms for cancer immunotherapy", International Journal of Nanomedicine 8: 1683-1696, 2013.

Swedish Search Report in Swedish Application No. 1650493-8, dated Apr. 12, 2016, 3 pages.

Thunberg et al., "Prolonged antigen-exposure with carbohydrate particle based vaccincation prevents aleergic immune responses in sensitized mice", Allergy 64: 919-926, 2009.

Uhlen et al., "Proteomics. Tissue-based map of the human proteome", Science 347 (6220): 1260419, 2015.

Zimmerman et al., "Simultaneous metal chelate affinity purification and endotoxin clearance for recombinant antibody fragments", Journal of Immuno, Methods 314: 67-73, 2006.

Gengoux et al., "In vivo induction of CD4 + T cell responses by antigens covalently linked to synthetic microspheres does not require adjuvant," International Immunology, 1995, 7:45-53.

Gregoriadis et al., "Vaccine Design The Role of Cytokine Networks," Dec. 31, 1997, p. 95.

Jenson et al., The biological activity of a recombinantly expressed (His)6-tagged peanut allergen (rAra h 1) is unaffected by endotoxin removal, Journal of Immunological Methods, 2008, 335:116-120.

Morita et al., "Antigen-specific immune response to endotoxin-free recombinant P34," Allergy, 2011, 66(7):985-986.

Sedlik et al. "Lack of Th1 OR Th2 polarization of CD4+ T cell response induced by particulate antigen targeted to phagocytic cells," 9(1):91-103.

Xie Baokang, editor, United Press of Beijing Medical University and Peking Union Medical University, Microbial Immunity and Nursing, Feb. 28, 1993, p. 1, Machine translation.

Bomhorst et al., "[16] Purification of proteins using polyhistidine affinity tags," Methods in enzymology, Jan. 1, 2000, 326:245-254.

Kimple et al., "Overview of affinity tags for protein purification," Current protocols in protein science, Aug. 2013, 73(1): 26 pages.

Kovacsovics-Bankowski, et al., "Efficient major histocompatibility complex class I presentation of exogenous antigen upon phagocytosis by macrophages," Proceedings of the National Academy of Sciences, Jun. 1, 1993, 90(11):4942-4946.

* cited by examiner

T-CELL REACTIVITY PLATFORM

CROSS-REFERENCE TO RELATED APPLICATIONS

This application is a § 371 U.S. National Stage Application of PCT/EP2016/081141, filed Dec. 15, 2016, which claims the benefit of Swedish Application Serial No. 1650493-8, filed on Apr. 12, 2016, and European Application Serial No. 15200619.3, filed Dec. 16, 2015. Priority is claimed to each of these applications, the entire contents of which are hereby incorporated by reference in their entireties.

TECHNICAL FIELD

The present invention relates to the field of diagnostic and analytic methods involving determination of antigen-specific T-cell activation.

BACKGROUND TO THE INVENTION

The adaptive immune system constitutes the branch of the immune system that can specifically adapt and respond to different pathogens or cell-damaging challenges encountered by the organism, as opposed to the innate immune system that responds in a more generic way. The adaptive system includes both humoral immunity, i.e. antibodies secreted by B-cells, and T-cell-mediated immunity. The specificity of the adaptive immune system lies in the B- and T-cell receptors expressed on B- and T-cells. Through an intricate system of mixing of gene segments the body produces an almost infinite variety of B- and T-cells, each expressing a specific receptor for a certain protein or peptide.

T-cells are lymphocytes that form a major part of the adaptive immune system, where they play a central role in cell-mediated immunity. The defining T-cell receptor (TCR) is expressed on the cell surface, and each receptor recognises an antigen derived peptide presented in the context of an MHC (major histocompatibility complex) molecule. Several types of T-cells exist, each having a distinct function in the cellular immune response.

Briefly, there are two main types of T-cells with different functions. The CD8-positive cytotoxic T-cell will bind peptides presented on the MHC class I receptor (in humans, termed human leukocyte antigen (HLA) class I) on a cell. All nucleated cells express HLA class I. If the presented peptide is considered as foreign (most often a sign of viral infection), the cytotoxic T-cell will kill the cell either by the protein Granzyme B or Perforin. The helper T-cell (Th), expressing the surface marker CD4, does not kill, rather it orchestrates immune responses by secretion of cytokines, proteins that will augment both pro-inflammatory and sometimes inhibitory signals between cells. Another important function of T-helper cells is to induce class switching of B-cells, e.g. to turn an IgM-secreting B-cell into an IgG-secreting cell, which will increase the humoral immune response against an antigen.

A T-helper cell will by way of its TCR bind its corresponding peptide presented on MHC-II (in humans, termed HLA class II), a receptor specifically expressed on so-called antigen presenting cells (APCs) or endothelial cells. The T-cell activation is dependent on the microenvironment where the Th-APC interaction takes place and the type of so-called co-stimulatory molecules that are expressed on the APC. The T-helper cell can differentiate into different Th-subsets, e.g. pro-inflammatory Th1, Th2, Th17 cells or to an inhibitory T-helper cell type called regulatory T-cells (Treg). The latter subset is of great importance to control immune responses, since an unrestrained immune system is harmful and can lead to tissue damage and autoimmunity.

Several methods suitable for determining antigen-specific T-cell activation exist, including ELISpot, Fluorospot, intracellular staining of cytokines with flow cytometry, FASCIA, proliferation assays (eg thymidine incorporation, CFSE or BrdU staining), specific TCR-detection with MHC-I or II tetramers, and ELISA- or Luminex analysis of secreted cytokines.

With the ELISpot technique, one directly detects release of a specific cytokine by cells in response to a stimulus. The cells are seeded on a membrane and the number of cytokine secreting cells is measured. Depending on which cytokine is being measured, different variables such as macrophage or T-cell activation can be measured. FluoroSpot builds upon the ELISpot technique and allows for simultaneous readings of several different secreted cytokines. This allows for a more exact and nuanced estimation of cell activation. Both of these methods offer a quick and easy way of measuring T-cell activation.

In recent years, large collections of recombinantly expressed proteins, i.e. proteins created with cloning techniques and bacterial or mammalian expression systems, have been produced by large-scale efforts such as the Human Atlas Project. The inventors have come to the realization that it would be of significant scientific and practical interest to be able to screen such polypeptide collections for antigens that are specifically T-cell activating. For instance, it would be of interest to screen T-cell samples from patients affected e.g. by an autoimmune disease, neoplastic disease, allergy or an infectious disease against a polypeptide library, to determine which epitopes the patient's T-cells are reacting to. Current methods are generally focused on determining which epitopes the patient's immune system is producing antibodies against (i.e. humoral response), failing to provide relevant information on a major part of the adaptive immune system, T-cell mediated immunity. Thus, being able to determine in large scale the antigens resulting in T-cell activation in a patient or a group of patients could tap into a new pool of novel biomarkers for the diseases, enable better diagnosis, support monitoring of disease progression in a patient, help identify therapeutic targets, etc.

For practical reasons the large polypeptide collections that exist today are usually made up of *E. coli* expressed proteins, and therefore contain substantial amounts of endotoxins derived from the host cell outer membrane. Due to environmental contamination, even polypeptide collections prepared in eukaryotic hosts or prepared by non-biological peptide synthesis contain practically significant levels of endotoxin. In the preparation of large collections, it is unpractical to establish a process that eliminates endotoxins to levels below detection, since endotoxins tend to bind to the proteins and are often difficult to remove once they contaminate a polypeptide sample.

Unfortunately, a common problem with assays determining T-cell activation is that even low levels of endotoxins that come into contact with the T-cells result in an activation masking the normally very low level of antigen-specific activation. Only a small fraction of the T-cell population being tested reacts in an antigen-specific manner to a given antigen (in the order of $1/10000$ in blood from a subject that has recently encountered the antigen), whereas a large fraction of the cells will respond to endotoxins creating a high level of background. Given the ubiquitous endotoxin contamination it is not feasible to perform the screening outlined above with the current polypeptide collections.

Thus, there is still need in the art for methods for assaying antigen-specific T-cell activation able to tolerate endotoxin contamination in the candidate antigen preparation, enabling screening of large polypeptide collections. It is an object of the present invention to provide improved methods and means for assaying antigen-specific T-cell activation.

Definitions

Endotoxins, e.g. Lipopolysaccharide (LPS), comprise covalently linked lipid and polysaccharide subunits found on the outer cell wall of gram-negative bacteria, such as *Escherichia coli*.

$CD4^+$ T-cell or T-helper cells are cells that orchestrate immune responses through cytokine secretion. They can both suppress or potentiate other immune cells such as stimulate antibody class switching of B-cells, expansion of cytotoxic T-cells or potentiate phagocytes. They get activated by antigen presentation via MHC class II on APCs and they express a T-cell receptor (TCR) specific for a stretch of approximately 15 amino acids (a so-called T-cell epitope) within a particular antigen.

$CD8^+$ T-cell or cytotoxic T-cells are cells that kill tumour cells, infected cells or cells otherwise damaged. Unlike $CD4^+$ T-cells they do not need APCs for activation. Their T-cell receptor recognizes antigen derived peptides (approximately 9-11 amino acids long) presented by MHC class I, a protein expressed on all nucleated cells.

Antigen-specific T-cell activation is a process requiring interaction between the TCR and a defined peptide presented on a MHC (HLA) molecule in combination with co-stimulation.

Protein Epitope Signature Tag (PrEST): Recombinantly produced peptides, which are fragments of proteins from a host (such as a human), representing unique peptide sequences of the protein they derive from. (See Lindskog M, Rockberg J, Uhlen M, Sterky F. *Selection of protein epitopes for antibody production. Biotechniques.* 2005; 38(5):723-7)

Antigen-presenting cells (APC) are typically dendritic cells (DCs), B-cells or macrophages, cells that either phagocyte or internalise extra-cellular organisms or proteins, i.e. antigens, and after processing present antigen-derived peptides on MHC class II to $CD4^+$ T-cells. In blood, monocytes are the most abundant antigen-presenting cells.

A phagocytable particle is defined as a particle able to be phagocytosed by cells of the immune system, in particular monocytes.

Peripheral blood mononuclear cells, PBMC, is a fraction of human blood prepared by density gradient centrifugation of whole blood. The PBMC fraction mainly consists of lymphocytes (70-90%) and monocytes (10-30%), while red blood cells, granulocytes and plasma have been removed.

SUMMARY OF THE INVENTION

The present invention relates to the following items. The subject matter disclosed in the items below should be regarded disclosed in the same manner as if the subject matter were disclosed in patent claims.

1. A method for assaying antigen-specific T-cell activation, comprising the steps of:
   a. Providing a phagocytable particle, having a candidate antigen polypeptide tightly associated thereto, wherein the particle with the associated polypeptide has been subjected to a denaturing wash resulting in an endotoxin level low enough to not interfere with the subsequent steps;
   b. Providing a viable antigen-presenting cell;
   c. Contacting the washed particle with the antigen-presenting cell in vitro under conditions allowing phagocytosis of the particle by the antigen-presenting cell;
   d. Providing a T-cell sample to be assayed comprising viable T-cells;
   e. Contacting the T-cell sample with the antigen-presenting cell contacted with the particle in vitro under conditions allowing specific activation of T-cells in response to an antigen presented by an antigen-presenting cell; and
   f. Determining the degree of T-cell activation in the T-cell sample.

2. The method according to item 1, wherein the method further comprises the steps (a') tightly associating a candidate polypeptide to a phagocytable particle and/or (a") subjecting a candidate antigen associated with a particle to a denaturing wash.

3. A method for assaying antigen-specific T-cell activation, comprising the steps of:
   a. Providing a phagocytable particle;
   b. Tightly associating a candidate antigen polypeptide to the particle;

c. Subjecting the particle with the associated polypeptide to a denaturing wash resulting in an endotoxin level low enough to not interfere with the subsequent steps;
d. Providing a viable antigen-presenting cell;
e. Contacting the washed particle with the antigen-presenting cell in vitro under conditions allowing phagocytosis of the particle by the antigen-presenting cell;
f. Providing a T-cell sample to be assayed comprising viable T-cells;
g. Contacting the T-cell sample with the antigen-presenting cell contacted with the particle in vitro under conditions allowing specific activation of T-cells in response to an antigen presented by an antigen-presenting cell; and
h. Determining the degree of T-cell activation in the T-cell sample.

4. The method according to any of the preceding items, further comprising the step of comparing the degree of T-cell activation to a relevant reference, whereby a higher degree of T-cell activation in the sample compared to the reference is indicative of the conclusion that the candidate antigen results in antigen-specific T-cell activation in the sample.

5. The method according to any of the preceding items, wherein determining the degree of T-cell activation in the T-cell sample involves determining the fraction of activated T-cells in the sample.

6. The method according to any of the preceding items, wherein several candidate antigens are assayed against the same T-cell sample.

7. The method according to any of the preceding items, wherein at least 10 candidate antigens are assayed against the same T-cell sample.

8. The method according to any of the preceding items, wherein the particle has a largest dimension of less than 5.6 µm, preferably less than 4 µm, more preferably less than 3 µm, even more preferably in the interval 0.5-2 µm or most preferably about 1 µm.

9. The method according to item 8, wherein the particle is substantially spherical.

10. The method according to any of the preceding items, wherein the denaturing wash involves subjecting the particle with the associated polypeptide to a high pH, such as at least pH 13, more preferably at least pH 14, most preferably at least pH 14.3.

11. The method according to any of the preceding items, wherein the denaturing wash involves subjecting the particle with the associated polypeptide to a low pH.

12. The method according to any of the preceding items, wherein the denaturing wash involves subjecting the particle with the associated polypeptide to a high temperature, such as at least 90° C., more preferably at least 92° C., most preferably at least 95° C.

13. The method according to any of the preceding items, wherein the denaturing wash involves subjecting the particle with the associated polypeptide to a denaturing agent, such as urea or guanidine hydrochloride at a sufficient concentration, such as at least 5M, 6M, 7M or 8M.

14. The method according to any of the preceding items, wherein the denaturing wash results in an endotoxin amount in the antigen being such that in the T-cell activation assay, the final concentration of endotoxin is less than 100 pg/ml, preferably less than 50 pg/ml, more preferably less than 25 pg/ml and most preferably less than 10 pg/ml.

15. The method according to any of the preceding items, wherein the particle has paramagnetic properties.

16. The method according to any of the preceding items, wherein the candidate antigen polypeptide is covalently linked to the particle.

17. The method according to any of the preceding items, wherein the candidate antigen polypeptide is linked to the particle via a metal chelate.

18. The method according to any of the preceding items, wherein the antigen-presenting cell and the T-cell sample are derived from the same individual.

19. The method according to any of the preceding items, wherein the antigen-presenting cell and the T-cell sample are derived from the same blood sample.

20. The method according to any of the preceding items, wherein the antigen-presenting cell and the T-cell sample are derived from a PBMC-sample from the same individual.

21. The method according to item 20, wherein the PBMC sample is fresh or has been subjected to freezing.

22. The method according to any of items 1-18, wherein the T-cell sample is derived from a tumour, preferably a lymphatic vessel in a tumour.

23. The method according to any of items 1-18, wherein the T-cell sample is derived from ascites.

24. The method according to any of the preceding items, wherein the T-cell sample comprises CD4+ and/or CD8+ T-cells.

25. The method according to any of the preceding items, wherein the washed particle, the antigen presenting cell and the T-cell sample are contacted concurrently.

26. The method according to any of the preceding items, wherein determining the degree of T-cell activation in the T-cell sample comprises determining the fraction of T-cells contacted with the antigen-presenting cell responding by secretion of IFN-γ, IL-17, IL-22 or a combination thereof.

27. The method according to any of the preceding items, wherein the method is for diagnosing multiple sclerosis, or following the course of multiple sclerosis, and involves determining the degree of T-cell activation in the T-cell sample comprises determining the fraction of T-cells contacted with the antigen-presenting cell responding by secretion of IL-17 and/or IL-22.

28. The method according to any of the preceding items, wherein determining the degree of T-cell activation in the T-cell sample is performed using an ELISpot or a FluoroSpot-technique.

29. The method according to any of the preceding items, wherein the candidate antigen polypeptide comprises at least 50 amino-acids, preferably at least 75 amino-acids, most preferably at least 100 amino-acids.

30. The method according to any of the preceding items, wherein the candidate antigen polypeptide is in form of a Protein Epitope Signature Tag (PrEST).

31. The method according to any of the preceding items, wherein the T-cell sample is from a human and the candidate antigen polypeptide sequence is derived from a human.

32. The method according to any of the preceding items, wherein the candidate antigen polypeptide is derived from an antigen known or suspected to be associated with disease.

33. The method according to any of the preceding items, wherein the candidate antigen polypeptide is derived from a polypeptide being:
   a. known to be highly expressed in a tissue or cell affected in an autoimmune disease;
   b. known to be associated with a neoplastic disease;
   c. known to be associated with an autoimmune disease;
   d. known to be associated with an infectious disease; or
   e. known to be associated with allergy or similar hypersensitivity.
34. A method for according to any of the preceding items, for diagnosing autoreactivity in a test subject comprising the steps of:
   a. Providing a phagocytable particle, having a candidate peptide auto-antigen tightly associated thereto, wherein the particle with the associated polypeptide has been subjected to a denaturing wash resulting in an endotoxin level low enough to not interfere with the subsequent steps;
   b. Providing a peripheral blood mononuclear cell (PBMC) sample from the test subject comprising viable T-cells and viable antigen-presenting cells;
   c. Contacting the PBMC sample with the particle in vitro under conditions allowing phagocytosis of the particle by an antigen-presenting cell and allowing specific activation of T-cells in response to an antigen presented by an antigen-presenting cell;
   d. Quantitating the fraction of activated T-cells in the contacted PBMC sample; and
   e. Comparing the quantitated fraction to comparably quantitated fraction from a healthy subject, whereby higher fraction of activated T-cells in the test subject is indicative of autoreactivity against the candidate auto-antigen in the test subject.

DETAILED DESCRIPTION

The present invention provides methods and means for assaying antigen-specific T-cell activation as disclosed in more detail below. By solving the problem associated with using endotoxin-contaminated polypeptides in an assay to antigen-specific T-cell activation, the methods and means enable and facilitate large-scale screening of new and existing polypeptide collections for biomarker discovery, diagnosis, monitoring of disease progression in patients, identification of therapeutic targets, etc.

Methods for Assaying Antigen-Specific T-Cell Activation

In a first aspect, the present invention provides an in vitro method for assaying antigen-specific T-cell activation, comprising the steps of:
   a. Providing a phagocytable particle, having a candidate antigen polypeptide tightly associated thereto, wherein the particle with the associated polypeptide has been subjected to a denaturing wash resulting in an endotoxin level low enough to not interfere with any of the subsequent steps (b-f) of the method;
   b. Providing a viable antigen-presenting cell (APC);
   c. Contacting the washed particle with the antigen-presenting cell contacted with the particle in vitro under conditions allowing phagocytosis of the particle by the antigen-presenting cell;
   d. Providing a T-cell sample to be assayed comprising viable T-cells;
   e. Contacting the T-cell sample with the antigen-presenting cell in vitro under conditions allowing specific activation of T-cells in response to an antigen presented by an antigen-presenting cell; and
   f. Determining the degree of T-cell activation in the T-cell sample.

The method further may comprise the steps of (a') tightly associating a candidate polypeptide to a phagocytable particle and/or (a") subjecting a candidate antigen associated with a particle to a denaturing wash. Thus, the method of the first aspect may comprise the steps of:
   a. Providing a phagocytable particle;
   b. Tightly associating a candidate antigen polypeptide to the particle;
   c. Subjecting the particle with the associated polypeptide to a denaturing wash resulting in an endotoxin level low enough to not interfere with any of the subsequent steps (d-h) of the method;
   d. Providing a viable antigen-presenting cell;
   e. Contacting the washed particle with the antigen-presenting cell in vitro under conditions allowing phagocytosis of the particle by the antigen-presenting cell;
   f. Providing a T-cell sample to be assayed comprising viable T-cells;
   g. Contacting the T-cell sample with the antigen-presenting cell contacted with the particle in vitro under conditions allowing specific activation of T-cells in response to an antigen presented by an antigen-presenting cell; and
   h. Determining the degree of T-cell activation in the T-cell sample.

The washed particle, the antigen presenting cell and the T-cell sample may be contacted concurrently, in the same container. For the conditions to allow antigen-specific activation of the cells, the conditions in the step of contacting the T-cell sample with the antigen-presenting cell contacted with the particle must be such that the background from non-antigen specific T-cell activation is low enough to not interfere with the assay.

Candidate Antigen Polypeptide

The candidate antigen polypeptide preferably comprises at least 50 amino-acids, even more preferably at least 75 amino-acids, most preferably at least 100 amino-acids. The candidate antigen polypeptide may be in form of a Protein Epitope Signature Tag (PrEST). Large protein libraries consisting of PrESTs already exist, for example the library created within the Human Atlas Project (Uhlen M, Fagerberg L, Hallstrom B M, Lindskog C, Oksvold P, Mardinoglu A, et al. *Proteomics*. Tissue-based map of the human proteome. Science. 2015; 347(6220):1260419). PrESTs contain amino-acid sequences unique for the corresponding full length protein, and have been used in the large scale Human Atlas Project for generating antibodies to most human proteins. The use of several PrESTs for the same human protein increases the chance of finding relevant T-cell epitopes. The antigen polypeptides being larger than the fragments presented by APCs also ensures that a wide variety of epitopes of each antigen will be presented, since the degradation of the antigen by the APCs is not a uniform process. In other words, the use of polypeptide antigens being of certain size is enabled by utilizing the phagocytic route of the APCs and allows improved detection of antigens with use of fewer antigen polypeptides, as opposed to presenting the antigens in short peptides that are capable of binding to MCH-receptors directly without cellular processing.

The candidate antigen polypeptide may be derived from an antigen known or suspected to be associated with disease. For example, the candidate antigen polypeptide is derived from a polypeptide being:

a. known to be highly expressed in a tissue or cell affected in an autoimmune disease; Examples being Proinsulin, Myelin-associated proteins.
b. known to be associated with a neoplastic disease; Examples being Estrogen receptor, Epidermal growth factor receptor, Cyclin-dependent kinase 1.
c. known to be associated with an autoimmune disease; Examples: Myelin Oligodendrocyte Protein, Myelin Basic Protein, Transaldolase.
d. known to be associated with an infectious disease; Examples: Viral capsid antigen, bacterial enterotoxins.
e. known to be associated with allergy or similar hypersensitivity; Examples: Can f 1, Equ c 1, Fel d 1.
f. a known tumour antigen; a neoantigen formed by common mutations in e.g. p53, ERBB2 (Erb-B2 Receptor Tyrosine kinase 2), PIK3CA (Phosphatidylinositol-4,5-bisphosphate 3-kinase)
g. a known modified protein, such citrullinated, variant, or phosphorylated protein.

The T-cell sample and the candidate antigen polypeptide are derived from the same species or from a different species. For instance, for studying autoimmunity or neoplastic disease, the T-cell sample and the candidate antigen polypeptide are preferably derived from the same species. For studying infectious disease, the T-cell sample is from the host whereas the candidate antigen polypeptide is derived from a pathogen of interest. For studying allergy or similar hypersensitivity, the T-cell sample is from the subject of interest whereas the candidate antigen polypeptide is derived from a different species known or suspected to elicit allergic or other hypersensitive reaction in the subject.

The T-cell sample may be from a human and the candidate antigen polypeptide sequence may be derived from a human.

Particle Properties

The particle is phagocytable by the antigen-presenting cell (APC; discussed below). The APCs can phagocytose particles of many different materials and shapes. In contrast, the size of the particles is limiting for phagocytosis. Too small of a size and the cells will not be triggered to phagocytose the particle. Too large of a size and the cell will not be able to phagocytose the particle as it will not fit in the cell.

The particles may have a largest dimension of less than 5.6 µm, preferably less than 4 µm, more preferably less than 3 µm, even more preferably in the interval 0.5-2 µm or most preferably about 1 µm. The particles may be substantially spherical, in which case the dimensions would refer to diameter.

Size similar to that of bacteria facilitates complete phagocytosis by APCs. This to ensure the antigen gets degraded by APCs and subsequently presented to T-cells via MHCII. The optimal size depends on the type of specific APC and can be determined by routine experimentation (see Example 5, FIG. 5)

The particle may have paramagnetic properties, which facilitates the denaturing wash discussed below by permitting the particles to be collected and/or held in place by a magnet. However, it is also possible to perform the washes by other means, such as by holding the particles in a column, or sedimenting the particles by gravity or by centrifugation.

Association of the Antigen Polypeptide and the Particle

The antigen polypeptide is associated to the particle in a manner that allows performing a denaturing wash as discussed below without dissociating the antigen from the particle.

One possible way of associating the polypeptide to the particle is shown in Example 1. However, the precise manner of association is not critical for the methods of the invention. Preferably, the candidate antigen polypeptide is covalently linked to the particle. Alternatively, the candidate antigen polypeptide may be linked to the particles via a metal chelate.

For example, particles linked with a metal chelating ligand, such as iminodiacetic acid can bind metal ions such as $Cu^{2+}$, $Zn^{2+}$, $Ca^{2+}$, $Co^{2+}$ or $Fe^{3+}$. These metal chelates can in turn bind proteins and peptides containing for example histidine or cystein with great strength. Thus, particles with metal chelates can non-covalently adsorb peptides/proteins, in a manner which allows stringent washing to reduce the amount of LPS and other contaminating components in the bound peptides/proteins.

Denaturing Wash

The denaturing wash is performed to reduce the level of endotoxin in the candidate antigen polypeptide to a level that does not interfere with the later step of determining the degree of antigen-specific T-cell activation.

Since endotoxins associate tightly with polypeptides, performing a denaturing wash which by definition at least transiently disrupts the secondary and tertiary structure is highly advantageous and in many cases essential to dissociate the endotoxin from the polypeptide. In the present application, even very low quantities of endotoxin cause interference.

The antigen-presenting cells will after uptake degrade the antigen polypeptide to small fragments, thus both transient and irreversible denaturation (disruption of the 3D-structure) can be tolerated. Association with the particles as disclosed by the present invention allow the handling of denatured proteins which may otherwise become insoluble or aggregate.

Figure 1:
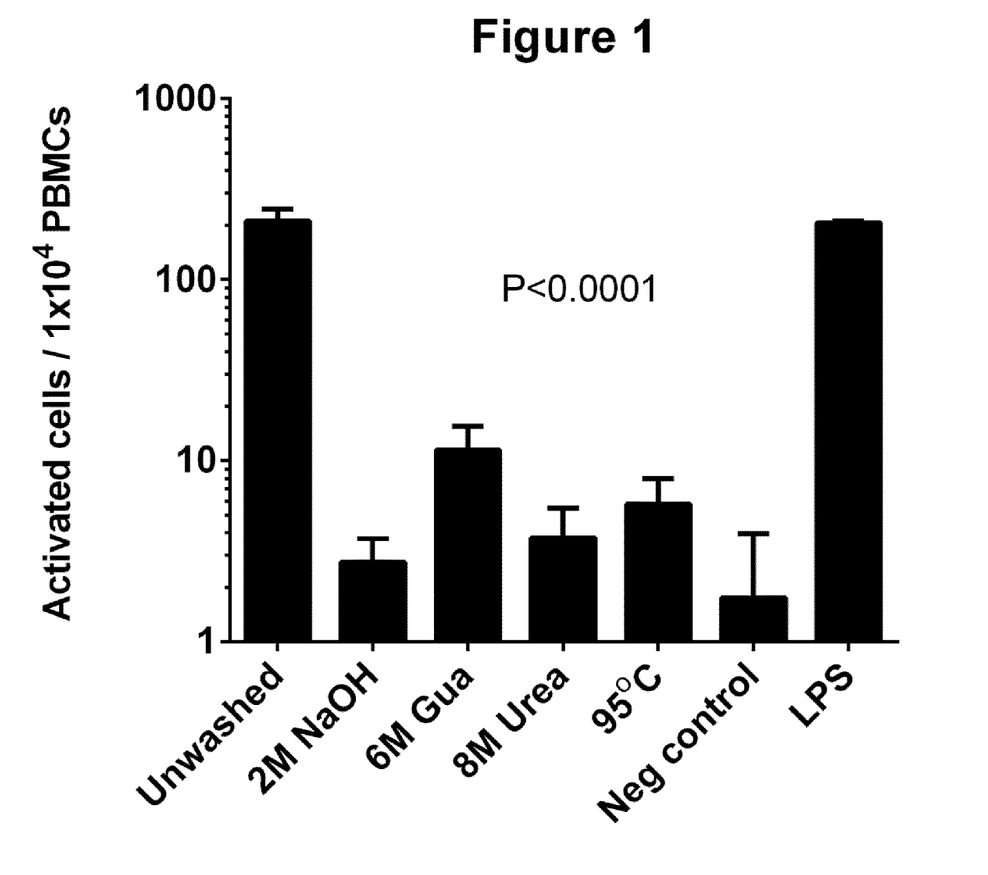
FIG. 1. Comparison of different washes for endotoxin removal. Monocyte activity in response to protein coupled beads subjected to different washes was assessed, comparing the effectiveness of different denaturing washes to non-washed beads. Lower activation is desirable. P-value determined using one-way ANOVA. Staples denote SD.

As shown in Example 2 and FIG. 1, the particular manner of denaturing wash is not critical in the context of the present invention. For instance, the denaturing wash may involve subjecting the associated polypeptide to a high pH, to a low pH, to a high temperature, to a denaturing agent or a combination thereof. Preferably, the denaturing wash involves subjecting the associated polypeptide to a high pH or to a strong denaturing agent such as 8M urea or 6M guanidine-HCl. Most preferably, the denaturing wash involves subjecting the associated polypeptide to a high pH of at least 13.0, more preferably at least 14.0, most preferably at least 14.3. The denaturing may involve subjecting the associated polypeptide to a wash with 1-5M, preferably 1-3M, more preferably 1.5-2.5M, most preferably 2M strong alkali, such as NaOH or KOH, preferably NaOH.

A particular advantage with a denaturing wash is that the conditions may be selected such that the preparation with the particles and the associated polypeptides is sterilized. If the preparation is contaminated with viable microorganisms, the subsequent steps in cell culture are likely to be compromised. In particular, high pH wash (e.g. pH >14) can conveniently simultaneously and quickly sterilize the preparation and achieve a denaturing wash effective in eliminating endotoxins.

Advantageously, the denaturing wash is such that it degrades or inactivates endotoxins, in addition to flushing them away. High pH wash (e.g. pH >14) has an inactivating effect on endotoxins.

The wash may comprise a single wash or several repeated washes, such as 2, 3, 4 or 5 washes.

The denaturing wash must result in an endotoxin level in the candidate antigen polypeptide that is compatible with a method for assaying antigen-specific T-cell activation as disclosed herein, such that the endotoxin does not result in a too high interference for the antigen-specific T-cell activation to be adequately detected. The level of remaining endotoxin may conveniently be tested using a monocyte activation assay (IL-1β/IL-6 FluoroSpot) as described herein in example 2. The tolerable level of endotoxin depends on the circumstances and in particular the antigen concentration. However, the endotoxin amount in the antigen preferably is such that in the T-cell activation assay, the final concentration of endotoxin is less than 100 pg/ml (i.e. 0-100 pg/ml), preferably less than 50 pg/ml, more preferably less than 25 pg/ml and most preferably less than 10 pg/ml. Methods for measuring endotoxin in a sample are known, for example the LAL assay.

Antigen-Presenting Cell (APC) and the T-Cell Sample

In the context of the present invention, the APC is a professional antigen presenting cell, such as a monocyte/macrophage or a dendritic cell. The APC may be a primary cell or an immortalized cell.

The APC must be compatible with the T-cells of the T-cell sample, such that they are capable of presenting antigens to the T-cells in an antigen-specific context (MHC restricted) that the T-cells can react to. The APC and the T-cell sample are preferably obtained from the same species and donor-matched with respect to MHC receptors. However, use of genetically engineered APCs from a different species is also envisioned.

If the antigen-presenting cell and the T-cell sample are derived from the same individual, any potential for a mismatch between the APC and the T-cells is avoided.

The antigen-presenting cell and the T-cell sample may be derived from the same blood sample, which is advantageous from a practical point of view. The antigen-presenting cell and the T-cell sample may be derived from a PBMC-sample from the same individual. Obtaining PBMC from peripheral blood samples is a routine protocol, which provides a handy source for both APCs and T-cells at the same time and from the same individual.

The PBMC sample may be freshly used or subjected to freezing. The possibility of using frozen cells is of great practical advantage from a logistical point of view.

The T-cell sample may be derived from a tumour, preferably a lymphatic vessel in a tumour.

The T-cell sample may also be derived from ascites.

The T-cell sample may comprise whole PBMCs including both CD4+ and CD8+ T-cells, purified T-cell populations, or PBMCs depleted of (a) particular T-cell population(s).

Determining the Degree of T-Cell Activation

The method may further comprise the step of comparing the degree of T-cell activation to a relevant reference, whereby a higher degree of T-cell activation in the sample compared to the reference leads to the conclusion that the candidate antigen results in antigen-specific T-cell activation in the sample. The reference is critical for defining "activation", so degree of activation is preferably defined in comparison to reference samples. The reference samples may for example be samples from normal healthy individuals when analysing patient samples, samples from normal tissue when analysing tumour or tumour draining lymph node samples or samples from before a treatment when following treatment effects. The reference samples are used to set the threshold for diagnostic/prognostic conclusion, and determine antigen specific positive i.e. activation, or negative i.e. downregulation.

Determining the degree of T-cell activation in the T-cell sample may involve determining the fraction of activated T-cells in the sample, i.e. the number of activated T-cells in relation to the total T-cells in the sample. The fraction of activated cells in relation to the fraction of activated cells in the reference sample will provide a measure of the magnitude of T-cell activation to specific antigens. Preferably, in each analysis the level of spontaneous activation ("background activation level") in individual samples is determined in samples incubated without antigen, i.e. negative control. The background activation may be compensated for in the analysis; in other words, fractions of activation may be calculated on net values where the fraction of activation to negative control is subtracted.

As shown in Example 3, determining the degree of T-cell activation in the T-cell sample may be performed using an ELISpot/FluoroSpot-technique or a proliferation assay (i.e thymidine incorporation). However, other assays and techniques suitable for the purpose are also known and may also be used. Determining the degree of T-cell activation in the T-cell sample may comprise determining the fraction of T-cells contacted with the antigen-presenting cell responding by secretion of Interferon gamma (IFN-γ), Interleukin 17 (IL-17), Interleukin 22 (IL-22) or a combination thereof, e.g. by means of an ELISpot or FluoroSpot assay. Other relevant analytes (combination(s) of cytokines) can be used for analysing specific diseases or conditions. For example, when analysing allergic patients, Th2 cytokines rather than Th1/Th17 cytokines may be analysed. T-reg cytokines may be of interest in cancer, allergy and when following vaccine treatments. Thus the FluoroSpot technique enables analysis of relevant activation profiles to various candidate antigen peptides in various conditions. This adds information on e.g. heterogeneity between patients, disease severity and progression.

As seen in Example 3, the determination of IL-17 and/or IL-22 secretion is surprisingly better than IFN-γ for differentiating MS patients from healthy controls. Thus, determining the degree of T-cell activation in the T-cell sample preferably comprises determining the fraction of T-cells contacted with the antigen-presenting cell responding by secretion of IL-17 and/or IL-22, and the method is for diagnosing multiple sclerosis, or following the course of multiple sclerosis. In other words, a T-cell sample derived from a subject having MS or suspected to have MS is preferably analysed for IL-17 and/or IL-22 secretion in response to candidate antigens.

Multiplex Analysis

As shown in Example 4, several candidate antigens may be assayed against the same T-cell sample. Preferably, at least 10 candidate antigens are assayed against the same T-cell sample. With the inventive method additional samples do not necessarily increase the laboratory work by much. Herein lies a strength of the inventive method, that it is easy to screen for a large number of antigens without much effort. An advantage of this is for example that being able to perform a large screening of possible autoantigens increases the chance of finding true autoantigens.

Diagnosing Autoreactivity

The method of the first aspect may be a method for diagnosing autoreactivity in a test subject comprising the steps of:
  a. Providing phagocytable particle, having a candidate peptide auto-antigen tightly associated thereto, wherein the particle with the associated polypeptide has been subjected to a denaturing wash resulting in an endotoxin level low enough to not interfere with the subsequent steps;

b. Providing a peripheral blood mononuclear cell (PBMC) sample from the test subject comprising viable T-cells and viable antigen-presenting cells;
c. Contacting the PBMC sample with the particle in vitro under conditions allowing phagocytosis of the particle by an antigen-presenting cell and allowing specific activation of T-cells in response to an antigen presented by an antigen-presenting cell;
d. Quantitating the fraction of activated T-cells in the contacted PBMC sample; and
e. Comparing the quantitated fraction to comparably quantitated fraction from a healthy subject, whereby higher fraction of activated T-cells in the test subject is indicative of autoreactivity against the candidate autoantigen in the test subject.

As shown in Example 4, the present invention provides a powerful tool to quickly screen for a large variety of autoantigens at the same time, and is not limited to MS. A screenable candidate library of proteins can readily be designed depending on disease and patients.

The method can be used for other inflammatory diseases in addition to autoimmune conditions, as long as antigen specific T-cells is a feature of the disease and the antigen library is adapted to the disease in question.

The term "comprising" is to be interpreted as including, but not being limited to. All references are hereby incorporated by reference. The arrangement of the present disclosure into sections with headings and subheadings is merely to improve legibility and is not to be interpreted limiting in any way, in particular, the division does not in any way preclude or limit combining features under different headings and subheadings with each other.

EXAMPLES

Example 1: Polypeptide Coupling to Beads

Covalently coupled polypeptides to beads containing free carboxylic acid groups. In this example Dynabeads® MyOne™ Carboxylic Acid (ThermoFischer Scientific) was used (1 μm diameter spheres). The bicinchoninic acid, BCA, protein assay was used to measure protein concentration before and after coupling to ensure successful coupling. Several polypeptides were tested and an average of 48.7 μg (mean: 48.7, SD: 20.5, N=10) was coupled per 1 mg beads. According to manufacturer's instruction, 50 μg polypeptide can be coupled per 1 mg beads, indicating that the efficiency of the coupling done in this example was high.

Example 2: Endotoxin Removal by Denaturing Washes

To test endotoxin removal with different types of denaturing washes, four different denaturing washing conditions were tested: (a) High pH (2M NaOH pH 14.3), (b) Heat (95° C.) and denaturing agents ((c) 8M Urea and (d) 6M guanidine hydrochloride). The level of remaining endotoxin was tested using a monocyte activation assay (IL-1β/IL-6 FluoroSpot) as monocyte activity is strongly increased by endotoxin and thus monocyte activation can be used for monitoring remaining LPS.

All tested types of denaturizing washes managed to significantly lower the amount of monocyte activation compared to the unwashed beads (see FIG. 1) (P<0.0001 for all washes). The denaturing washes were so effective the washed beads stimulated the cells to a degree comparable to that of the negative control. Wash with 2M NaOH resulted in the lowest amount of endotoxin, followed closely by 8M urea.

Example 3: T-Cell Activation Assays

FluoroSpot

Figure 3A:
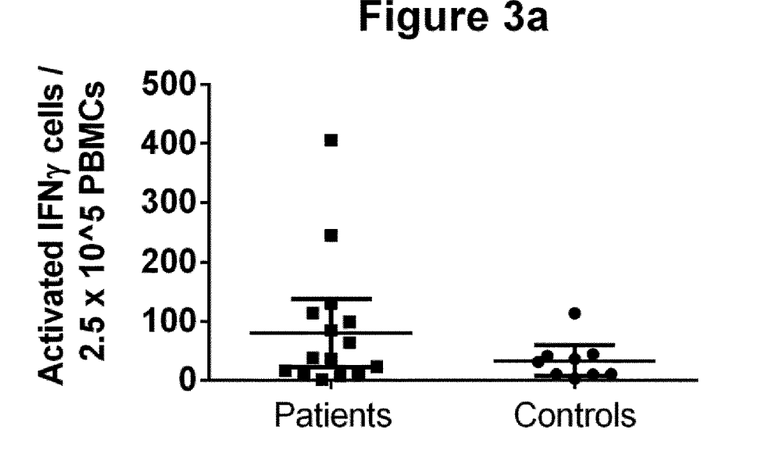
FIG. 3. IFNγ/IL-22/IL-17 Fluorospot assay comparing T-cell activation in multiple sclerosis (MS)-patients and healthy controls when stimulated with a suspected autoantigen in MS. P-values determined with Mann-Whitney-U test and written when found. Staples denote CI95% of mean.
Figure 3B:
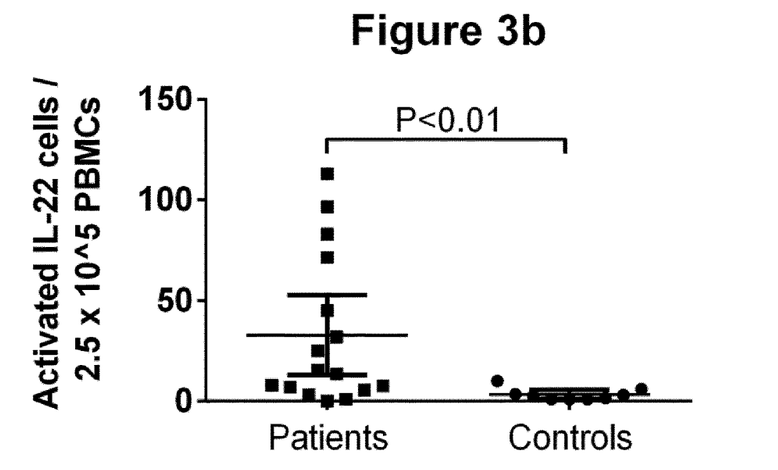
Figure 3C:
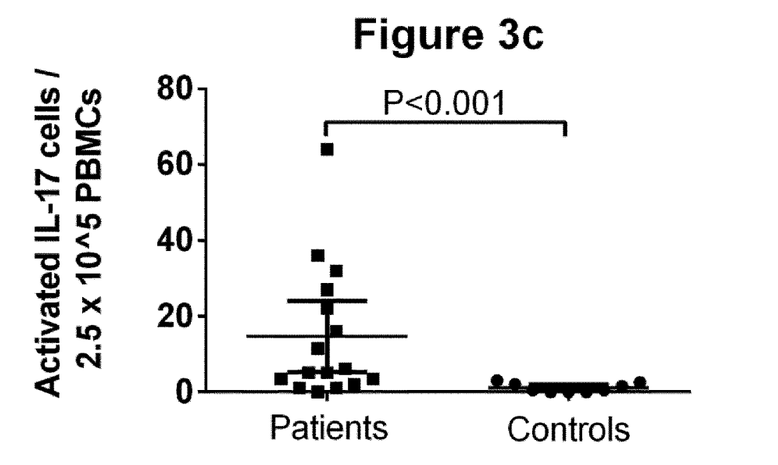

FluoroSpot assay was performed with samples from 16 Multiple Sclerosis Patients and 9 healthy controls. PBMCs from patients and controls were incubated together with a suspected autoantigen in the FluoroSpot plate. As seen in FIG. 3, several of the MS patients showed significantly higher number of activated cells (panel a). The MS patients had a mean number of 37.4 (95% CI 13.0-52.9) IL-22 secreting activated cells while the healthy controls had a mean number of 3.3 (95% CI 0.97-5.6) activated cells. P value of difference=0.0062. For IL-17 secreting activated cells the number was 14.7 (CI95% 5.3-24.1) in patients compared to 0.28 (CI95%-1.4-2.0), P value of difference <0.0007 (panel b). For IFNγ secreting cells however the difference was not statistically significant with a mean number of 80.0 (CI95% 22.3-138) for patients versus 33 (CI95% 7.1-59.0) P=0.495 for controls (panel c). Significance calculated using Mann-Whitney-U test.

These results show that the activation of T-cells with antigen coupled to beads can be measured with the FluoroSpot assay, and comparisons of patients vs. healthy controls can be made. Surprisingly the classic marker for T-cell activation, IFNγ, showed the weakest difference in the patient vs control comparison. Both IL-17 and IL-22 however showed a strong significant difference between patients and controls, indicating that these might be more suitable cytokines to analyse when looking for autoantigens in MS.

Proliferation Assay

Figure 2:
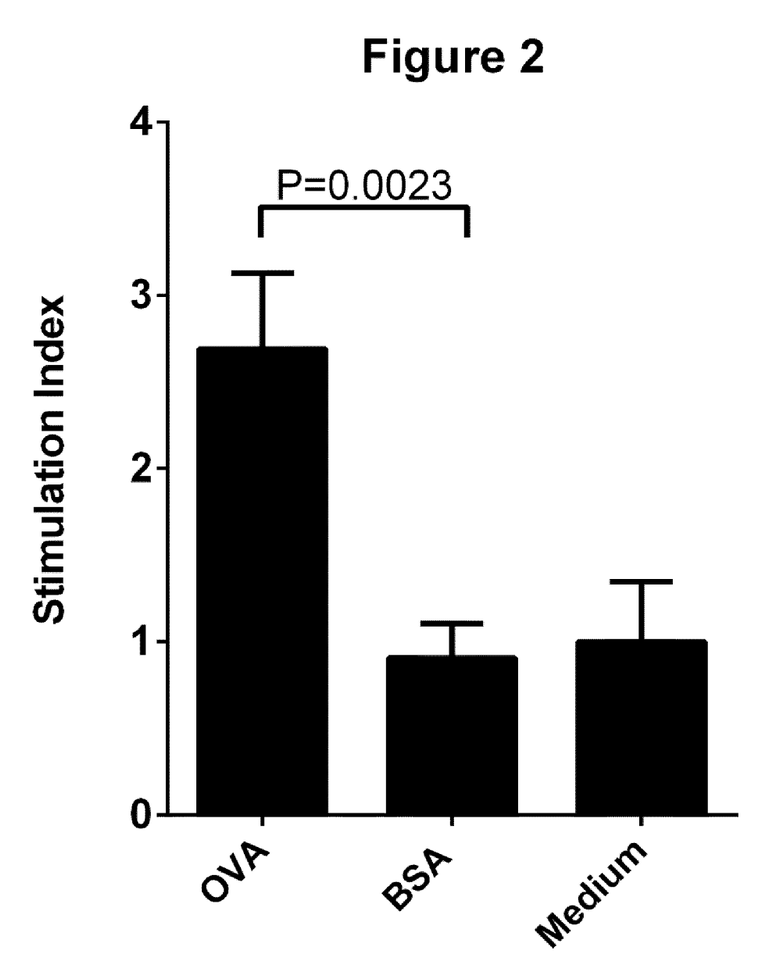
FIG. 2. Measurement of T-cell activation with a cell proliferation assay. Thymidine incorporation assay using splenocytes from ovalbumin sensitized mice. Comparison of ovalbumin coupled beads, bovine serum albumin coupled beads and medium. P-value determined with students T-test and indicated when p<0.05 found. Staples denote SD.

Proliferation assay with Thymidine incorporation. Splenocytes from ovalbumin (OVA) immunized mice were incubated with OVA or BSA coupled beads to measure antigen specific proliferation. The proliferation of the cells incubated with beads was expressed as stimulation index (SI). (As seen in FIG. 2 the cells incubated with OVA-beads had an increase in proliferation with an SI of 2.69 (95% CI 1.6-3.78, P<0.005). The cells incubated with BSA failed to give an increase in proliferation with an SI of 0.9 (95% CI 0.7-1.1, P=0.37).

These results show that the activation of immune cells (splenocytes in this example) with antigen coupled to beads can be measured by a proliferation assay. It also shows that the proliferation observed is antigen specific, as the OVA coupled beads stimulated proliferation, but the BSA coupled beads completely failed to induce proliferation. The experiment shows that antigen coupled to beads can be used for in vitro stimulation of antigen-specific T-cell proliferation. Thymidine incorporation is just one method to measure proliferation, other methods for measuring proliferation will thus also be applicable, e.g. CFSA dilution and BrdU incorporation assays.

Example 4: Autoantigen Screen in MS Against a Library of 125 Proteins

Identification of autoantigens in Multiple Sclerosis; Measuring T-cell activation to a large number of PrESTs coupled to beads, using IFNγ/IL-22/IL-17A FluoroSpot as assay for T-cell activation. A screening like this identifies possible autoantigens by detecting those antigens that stimulate a higher T-cell response in PBMCs from MS patients compared to healthy controls, and helps decide which antigen to analyse further.

Figure 4A:
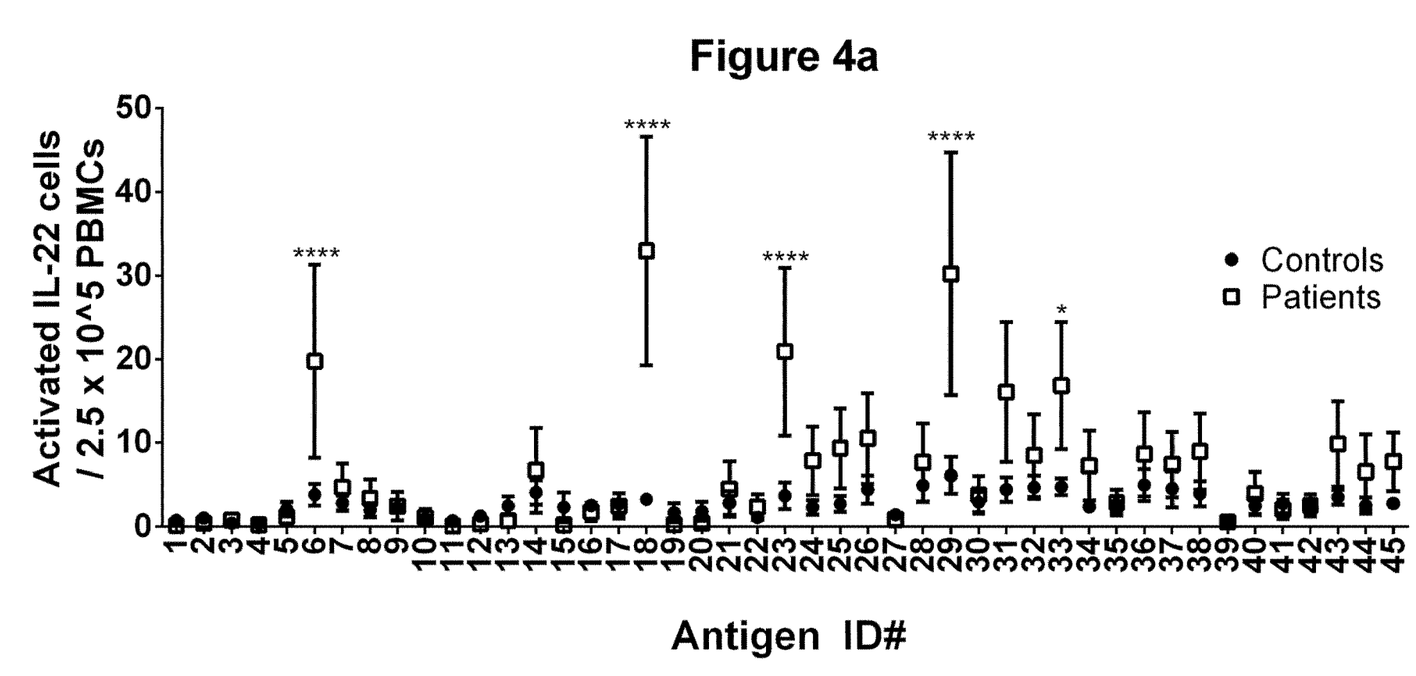
FIG. 4. Autoantigen screening in Multiple Sclerosis-patients against a library of 125 proteins. Comparison of the T-cell activation from MS-patients' PBMCs to that of PBMCs from healthy controls. Panel A, activation determination by IL22-FluoroSpot. Panel B, activation determination by IL17-FluoroSpot. Panel C, activation determination by IFNγ FluoroSpot. Patient's T-cells react significantly more to certain proteins in the library. Open squares and filled circles indicate mean activation in patients' and controls' PBMCs respectively, staples denote CI95% of mean. P-value determined using a two-way ANOVA. Asterisks denote P-value.
Figure 4B:
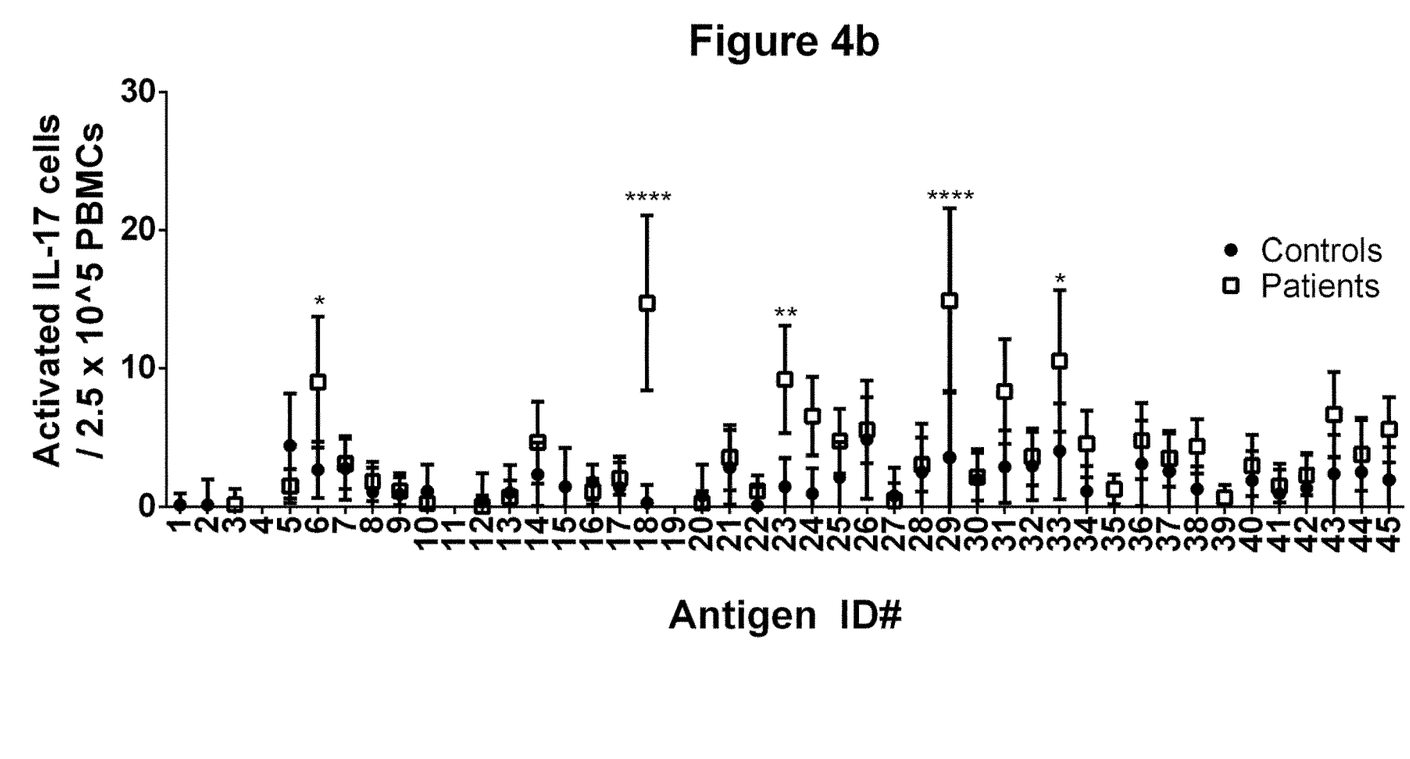
Figure 4C:
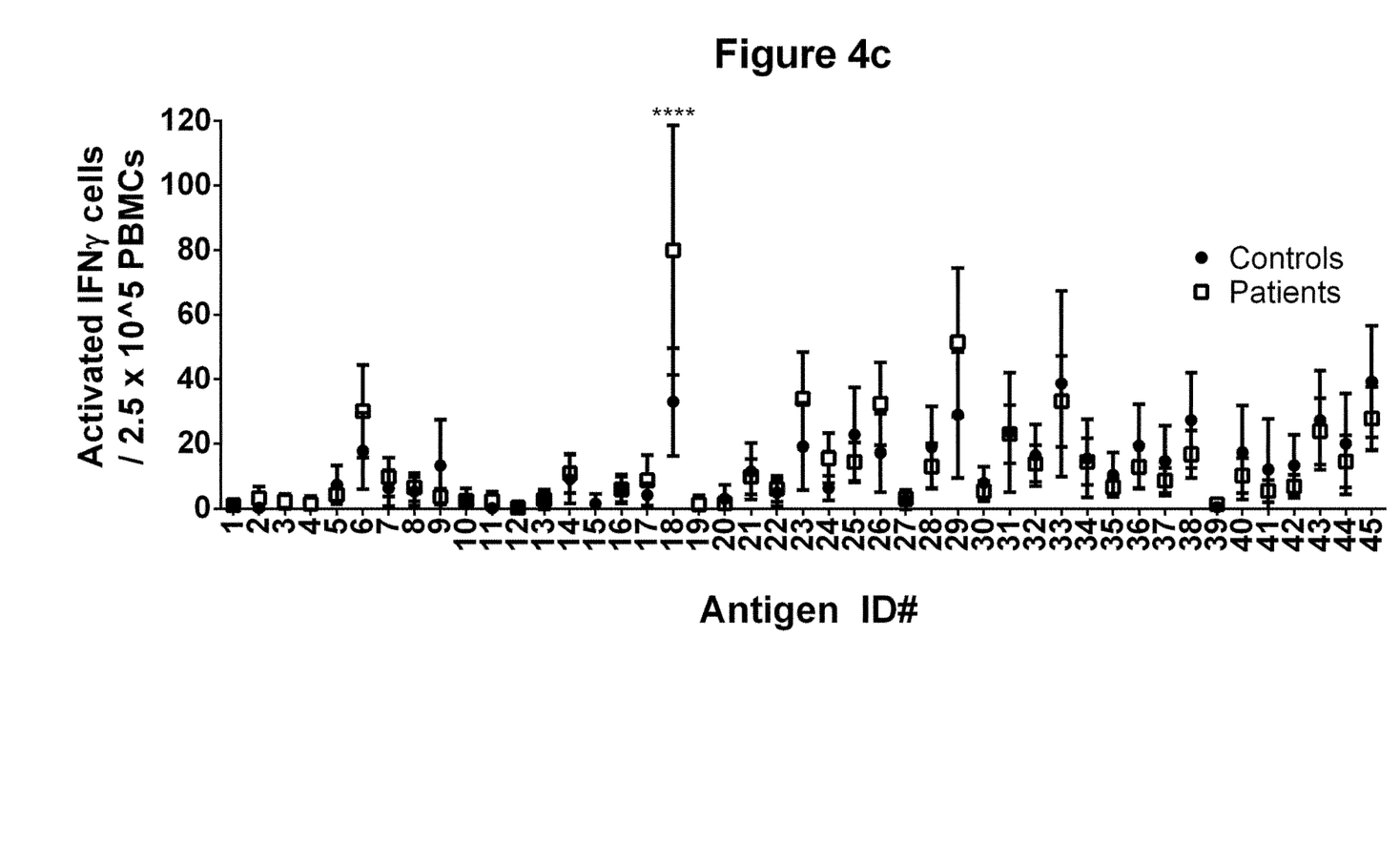

As seen in FIG. 4, in this screening of 16 patients and 9 healthy controls, statistically significant difference between mean patient and mean control number activated cells could be seen when analysed using a Two-Way ANOVA. For IL-22 secreting activated T-cells difference was seen for 5 antigens, antigen #6 (P<0.0001), antigen #18 (P<0.0001), antigen #23 (P<0.0001), antigen #29 (P<0.0001) and antigen #33 (P<0.05) (panel a). For IL-17 secreting T-cells a difference between patients and controls could be seen for the same 5 antigens, antigen #6 (P<0.05), antigen #18 (P<0.0001), antigen #23 (P<0.01), antigen #29 (P<0.0001) and antigen #33 (P<0.05) (panel b). For IFNγ a difference could be seen only for antigen #18 (p<0.0001) (panel c).

These results show that a method of the present invention can be used as an autoantigen screening, a tool to identify possible new autoantigens in MS.

Example 5: Identification of Suitable Bead Size for Phagocytable Beads

Figure 5:
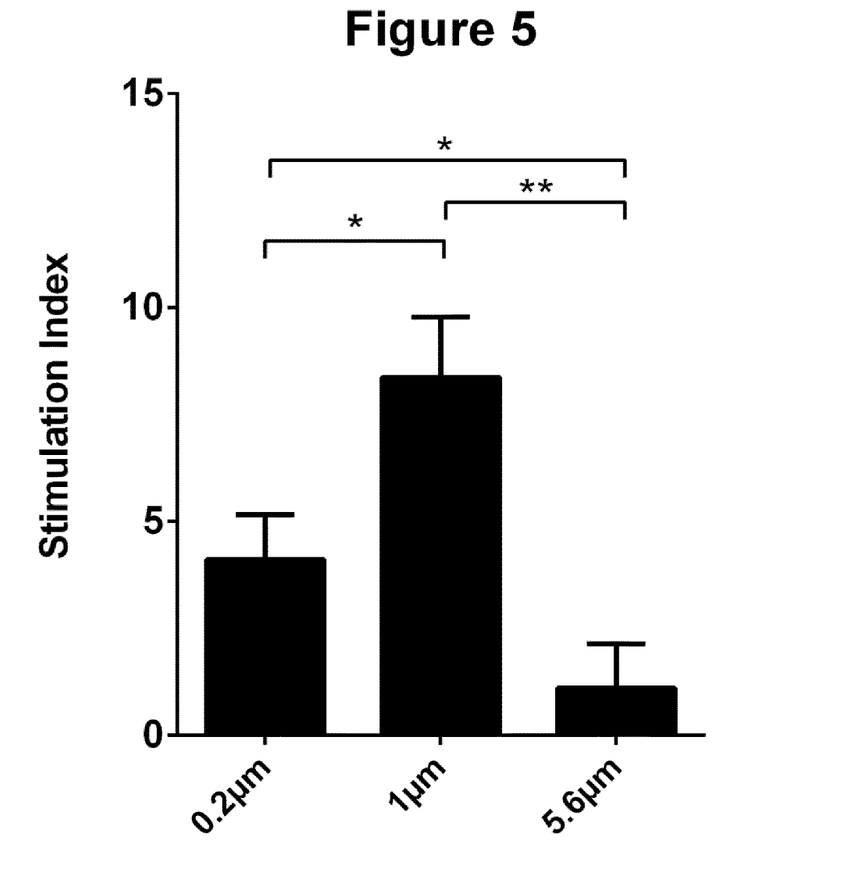
FIG. 5. Effect of bead size on T-cell activation. Proliferation assay (with thymidine incorporation) with splenocytes from ovalbumin sensitized mice. Comparison of ovalbumin coupled to differently sized beads with a diameter of 5.6 μm, 1 μm and 0.2 μm. P-values determined using students T-test and written indicated when p<0.05 found. Staples denote SD.

Proliferation assay with Thymidine incorporation was used to test the effect of bead size on antigen-specific T-cell activation. Splenocytes from ovalbumin (OVA) immunized mice were stimulated with OVA coupled beads of different sizes to measure antigen specific proliferation. As seen in FIG. 5, cells incubated with OVA-beads with a diameter of 0.2 µm showed increase in proliferation with a mean SI of 4.1 (95% CI 2.4-5.8, P=0.007). The cells incubated with OVA-beads with a diameter of 1 µm showed increase in proliferation with a mean SI of 8.4 (95% CI 6.1-10.6, P<0.005). The cells incubated with OVA-beads with a diameter of 5.6 µm failed to stimulate proliferation, mean SI 1.1 (95% CI 0.4-2.7, P=0.876). These results show that antigen coupled to beads of different sizes can stimulate cell proliferation. The beads with a diameter of about 1 µm seems to be most efficient in regards to cell stimulation but beads down to a size of 0.2 µm still works. It is reasonable to predict that beads of sizes larger than 1 µm also work, although as the diameter comes close to 5.6 µm the beads completely fail to stimulate the cells. It is reasonable to assume that 1 µm is an optimal size, since it is similar to the size of bacteria. Our immune system has evolved to phagocytose and react to microorganisms/particles of this size. A normal antigen presenting cell has a size in the range 10-15 µm.

Materials and Methods

Example 1

Covalent coupling of proteins to paramagnetic beads containing free carboxylic acid groups.

In this example Dynabeads® MyOne™ Carboxylic Acid with 1 µm diameter (ThermoFischer Scientific) were used and the coupling procedure was carried out according to the manufacturers protocol (Two-Step procedure using NHS (N-Hydroxysuccinimide) and EDC (ethyl carbodiimide)).

Beads were washed twice with MES-Buffer (25 mM MES (2-(N-morpholino)ethanesulfonic acid), pH 6). The carboxylic acid groups were then activated by adding 50 mg/ml NHS (N-Hydroxysuccinimide) and 50 mg/ml EDC (N-(3-Dimethylaminopropyl)-N'-ethylcarbodiimide) in MES-buffer to the beads and incubated for 30 minutes in room temperature. The beads were collected with a magnet and the supernatant was removed and the beads washed twice with MES-buffer. The protein was diluted in MES-buffer to a concentration of 1 mg/ml, total 100 ug and added to the beads and incubated for 1 h in room temperature. The beads were collected with a magnet and the supernatant was removed and saved for protein-concentration measurement. The non-reacted activated carboxylic acid groups were quenched with 50 mM Tris pH 7.4 for 15 minutes. The beads were then washed with PBS pH 7.4 and then stored in −80° C.

To measure the amount of protein coupled to the beads, a BCA protein assay kit (Pierce BCA Protein Assay Kit, ThermoFisher Scientific) was used to measure the protein concentration of the protein before coupling as well as in the supernatant after coupling. The BCA-assay was used according to the manufacturer's protocol.

Example 2

Endotoxin Removal by Denaturing Washes.

Beads were coupled with a recombinant protein produced in *E. coli*. The protein-coupled beads were washed at several different denaturing conditions to ensure removal of endotoxin. The remaining endotoxin was measured using a monocyte reactivity assay (IL1B/IL6 FluoroSpot-assay, MABTECH, Sweden).

For endotoxin removal, the beads were washed with one of 3 different wash-buffers, 2M NaOH pH 14.3, 8M Urea or 6 M Guanidine (Guanidine-HCl), all in sterile water at RT, or they were incubated in PBS at 95° C. The beads were suspended in the buffer and shaken for 4 min, collected with a magnet and the supernatant removed. This was repeated 3 times. The heat treated beads were put in PBS pH 7.4 and put in a heating block at 95° C. for 5 minutes, then collected with a magnet and the supernatant removed. This was repeated 3 times. The beads were then washed 3 times with sterile PBS to remove any remaining wash-buffer.

To measure endotoxin levels, a monocyte reactivity assay was used (IL-1β/IL-6 FluoroSpot-assay, MABTECH, Sweden). Peripheral blood mononuclear cells (PBMCs) were isolated by Ficoll-Paque (GE Healthcare, Uppsala, Sweden) gradient centrifugation. Cells were suspended in cRPMI (RPMI 1640 medium containing 10% fetal calf serum, 1% L-glutamine and 1% penicillin-streptamycin). 3,000,000 beads were added to each well in the FluoroSpot plate in quadruplicates for each type of bead and each type of wash. Unwashed beads, LPS and medium were used as controls. The cells were added to the FluoroSpot plate at a concentration of 10,000 and 5,000 cells in 200 µl cRPMI cells per well (2 wells of each cell concentration and each type of bead). The plate was incubated for 18 h in a humidified environment at 37° C. and 5% $CO_2$. The plate was then developed according to the manufacturer's protocol and read in a FluoroSpot-reader.

Example 3

FluoroSpot

The FluoroSpot assay for analyzing patient vs control T-cell activation versus a suspected autoantigen in MS was run with an IFNγ/IL17/IL22 FluoroSpot (MABTECH). The protocol was exactly as described in Example 4, although here just analyzing the response to one antigen instead of the whole library of 125 proteins.

Proliferation Assay

Proliferation assay with thymidine incorporation with splenocytes from ovalbumin sensitized mice. As stimuli, ovalbumin (SigmaAldrich) and BSA (SigmaAldrich) coupled to beads (Dynabeads® MyOne™ Carboxylic Acid) were used.

Mice were immunized to ovalbumin via monthly injections of 100 μg ovalbumin (Sigma) adsorbed to aluminium hydroxide. Three months after the first injection the mice were killed and spleens harvested. Splenocytes were prepared by standard procedures, as described in Thunberg et al. 2009, Allergy 64:919.

The cells were incubated in cRPMI either with ovalbumin coupled beads or BSA coupled beads (10 beads per cell) for 5 days. All cells were incubated for 6 days in a humidified atmosphere with 6% $CO_2$ at 37° C. One μCi/well [$^3$H] thymidine was added to cell cultures for the final 18 hours of incubation. Mean counts per minute (cpm) obtained from stimulated triplicates were divided by mean cpm values from un-stimulated cells and expressed as stimulation indices (SI). SI-values ≥2.0 are generally considered positive.

Example 4

An autoantigen screening against a library of 125 proteins in Multiple Sclerosis using protein coupled beads (Dynabeads® MyOne™ Carboxylic Acid (ThermoFischer Scientific)) as stimuli and FluoroSpot (IFNγ/IL17/IL22 FluoroSpot, MABTECH) as assay for measuring for T-cell activation.

Peripheral blood mononuclear cells (PBMCs) from a total of 18 multiple sclerosis patients and 9 healthy controls were used. The 125 different proteins consisted of a wide variety of human-specific PrESTs from the Human Atlas Project. The PrESTs were coupled to beads according to manufacturer's protocol (as described in example 1).

PBMCs were isolated from venous blood samples (taken in BD Vacutainer EDTA-tubes) by Ficoll-Paque (GE Healthcare, Uppsala, Sweden) gradient centrifugation according to standard protocol. The cells were frozen in freezing medium (45% FCS, 45% RPMI, 10% DMSO) and stored in −150° C.

The 125 different PrESTs were pooled into 45 different pools to fit the 96-well format of the FluoroSpot and subsequently washed in 2M NaOH to remove endotoxin (as described in Example 2). 3,000,000 beads were added to each well of the FluoroSpot plate, each different pool was run in duplicates. Anti-CD3 was used as positive control, medium only and medium with naked beads were used as negative controls.

The PBMCs were thawed in a water bath at 37° C. and washed in cRPMI (RPMI 1640, 10% FCS, 1% L-glut and 1% Penicillin-Streptavidin). 250,000 cells in 200 μl cRPMI were added to each well and the plate was then incubated for 44 h in a humidified environment at 37° C. and 5% $CO_2$. After incubation, the plate was developed according to the manufacturer's protocol (Mabtech) and read in a FluoroSpot reader.

Example 5

Splenocytes from Ovalbumin sensitized mice and Ovalbumin coupled beads were used to evaluate the effectiveness of differently sized beads. Paramagnetic beads with a diameter of 5.6 μm, 1 μm and 0.2 μm with carboxylic acid on their surface were coupled with ovalbumin or bovine serum albumin according to the protocol in Example 1.

To test the effectiveness of the beads to stimulate antigen specific T-cell activation a proliferation assay (with $^3$H thymidine incorporation) was used. Bead concentration in relation to cell concentration was 1:1 for the 5.6 μm beads, 10:1 for the 1 μm beads and 500:1 for the 0.2 μm beads. Total protein concentration during the incubation with the cells was calculated to 125 ng/ml, 160 ng/ml and 160 ng/ml for the 5.6 μm, 1 μm and 0.2 μm respectively. The proliferation assay was run the same way as in example 3.

The invention claimed is:

1. A method for assaying antigen-specific T-cell activation, comprising the steps of:
   a. providing a phagocytable particle, having a candidate antigen polypeptide associated by covalent linking, wherein the particle with the associated polypeptide has been subjected to a denaturing wash resulting in an endotoxin level low enough to not interfere with steps b-f;
   b. providing a viable antigen-presenting cell;
   c. contacting the washed particle with the antigen-presenting cell in vitro under conditions allowing phagocytosis of the particle by the antigen-presenting cell;
   d. providing a T-cell sample to be assayed, the T-cell sample comprising viable T-cells;
   e. contacting the T-cell sample with the antigen-presenting cell contacted with the particle in vitro under conditions allowing specific activation of T-cells in response to an antigen presented by an antigen-presenting cell; and
   f. determining the degree of T-cell activation in the T-cell sample.

2. A method for assaying antigen-specific T-cell activation, comprising the steps of:
   a. providing a phagocytable particle;
   b. associating by covalent linking a candidate antigen polypeptide to the particle;
   c. subjecting the particle with the associated polypeptide to a denaturing wash resulting in an endotoxin level low enough to not interfere with steps d-h;
   d. providing a viable antigen-presenting cell;
   e. contacting the washed particle with the antigen-presenting cell in vitro under conditions allowing phagocytosis of the particle by the antigen-presenting cell;
   f. providing a T-cell sample to be assayed, the T-cell sample comprising viable T-cells;
   g. contacting the T-cell sample with the antigen-presenting cell contacted with the particle in vitro under conditions allowing specific activation of T-cells in response to an antigen presented by an antigen-presenting cell; and
   h. determining the degree of T-cell activation in the T-cell sample.

3. The method according to claim 1, further comprising the step of comparing the degree of T-cell activation to a relevant reference, whereby a higher degree of T-cell activation in the sample compared to the reference indicates that the candidate antigen results in antigen-specific T-cell activation in the sample.

4. The method according to claim 1, wherein determining the degree of T-cell activation in the T-cell sample comprises determining the fraction of activated T-cells in the sample.

5. The method according to claim 1, wherein several candidate antigens are assayed against the same T-cell sample.

6. The method according to claim 5, wherein at least 10 candidate antigens are assayed against the same T-cell sample.

7. The method according to claim 1, wherein the antigen-presenting cell and the T-cell sample are derived from a single individual.

8. The method according to claim 7, wherein the antigen-presenting cell and the T-cell sample are derived from the same blood sample from the individual.

9. The method according to claim 7, wherein the antigen-presenting cell and the T cell sample are derived from a peripheral blood mononuclear cell (PBMC) sample from the individual.

10. The method according to claim 1, wherein the T-cell sample is derived from a tumour.

11. The method according to claim 1, wherein the T-cell sample is derived from ascites.

12. The method according to claim 1, wherein the T-cell sample comprises CD4$^+$T-cells, CD8$^+$T-cells, or both.

13. The method according to claim 1, wherein the washed particle, the antigen presenting cell and the T-cell sample are contacted concurrently.

14. The method according to claim 1, wherein determining the degree of T-cell activation in the T-cell sample comprises determining the fraction of T-cells contacted with the antigen-presenting cell responding by secretion of IFN-γ, IL-17, IL-22, or combinations thereof.

15. The method according to claim 1, wherein determining the degree of T-cell activation in the T-cell sample comprises determining the fraction of T-cells contacted with the antigen-presenting cell responding by secretion of IL-17, IL-22, or both.

16. The method according to claim 1, wherein the candidate antigen polypeptide comprises at least 50 amino acids.

17. The method according to claim 1, wherein the T-cell sample is from a human and the candidate antigen polypeptide sequence is derived from a human.

18. The method according to claim 1, wherein the candidate antigen polypeptide is derived from a polypeptide:
   a. known to be highly expressed in a tissue or cell affected in an autoimmune disease;
   b. known to be associated with a neoplastic disease;
   c. known to be associated with an autoimmune disease;
   d. known to be associated with an infectious disease; or
   e. known to be associated with allergy or similar hypersensitivity.

19. The method according to claim 1, comprising the steps of:
   a. providing a phagocytable particle, having a candidate peptide auto-antigen associated by covalently linking, wherein the particle with the associated polypeptide has been subjected to a denaturing wash resulting in an endotoxin level low enough to not interfere with steps b-e;
   b. providing a peripheral blood mononuclear cell (PBMC) sample from a test subject, the PBMC sample comprising viable T-cells and viable antigen-presenting cells;
   c. contacting the PBMC sample with the particle in vitro under conditions allowing phagocytosis of the particle by an antigen-presenting cell and allowing specific activation of T-cells in response to an antigen presented by an antigen-presenting cell;
   d. quantitating the fraction of activated T-cells in the contacted PBMC sample; and
   e. comparing the quantitated fraction to a comparable quantitated fraction from a healthy subject, wherein a higher fraction of activated T-cells in the test subject as compared to the healthy subject is indicative of autoreactivity against the candidate auto-antigen in the test subject.

* * * * *

UNITED STATES PATENT AND TRADEMARK OFFICE
CERTIFICATE OF CORRECTION

| | | |
|---|---|---|
| PATENT NO. | : 11,360,079 B2 | Page 1 of 1 |
| APPLICATION NO. | : 16/061611 | |
| DATED | : June 14, 2022 | |
| INVENTOR(S) | : Grönlund | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 786 days.

Signed and Sealed this
Twenty-fifth Day of July, 2023

Katherine Kelly Vidal
*Director of the United States Patent and Trademark Office*